(12) United States Patent
Hartlep et al.

(10) Patent No.: US 7,742,630 B2
(45) Date of Patent: Jun. 22, 2010

(54) METHOD AND APPARATUS FOR DETERMINING A BACKFLOW OF A SUBSTANCE

(75) Inventors: Andreas Hartlep, Naring (DE); Christoph Pedain, Munich (DE); Martin Brady, Baltimore, MD (US); Raghu Raghavan, Phoenix, MD (US)

(73) Assignee: BrainLAB AG, Feldkirchen (DE)

( * ) Notice: Subject to any disclaimer, the term of this patent is extended or adjusted under 35 U.S.C. 154(b) by 679 days.

(21) Appl. No.: 11/562,262

(22) Filed: Nov. 21, 2006

(65) Prior Publication Data

US 2008/0200804 A1    Aug. 21, 2008

Related U.S. Application Data

(60) Provisional application No. 60/754,508, filed on Dec. 28, 2005.

(30) Foreign Application Priority Data

Nov. 21, 2005    (EP)    ................................ 05025351

(51) Int. Cl.
G06K 9/00 (2006.01)
(52) U.S. Cl. .................................................... 382/128
(58) Field of Classification Search ......... 382/128–134; 604/30, 500; 600/431; 424/85.1; 128/920–930; 250/455–465; 356/39–49
See application file for complete search history.

(56) References Cited

U.S. PATENT DOCUMENTS 5,720,720 A    2/1998    Laske et al. ................. 604/500

| 6,549,803 | B1 | 4/2003 | Raghavan et al. ............. 604/30 |
| 6,572,579 | B1 | 6/2003 | Raghavan et al. ........... 600/431 |
| 2002/0114780 | A1 | 8/2002 | Bankiewicz et al. ....... 424/85.1 |
| 2005/0267360 | A1* | 12/2005 | Birkenbach et al. ......... 600/423 |
| 2009/0208422 | A1* | 8/2009 | Mardor et al. ........... 424/9.364 |

FOREIGN PATENT DOCUMENTS

WO    01/85027 A2    11/2001

OTHER PUBLICATIONS

Mardor, Y. et al., "Convection-Enhanced Drug Delivery: Increased Efficacy and Magnetic Resonance Image Monitoring", Cancer Research, vol. 65, No. 15, Aug. 2005, pp. 6858-6863.
Morrison, P.F., et al., "Focal Delivery during direct infusion to brain: Role of flow rate, catheter diameter, and tissue mechanics", American Journal of Physiology—Regulatory Integrative and Comparative Physiology, vol. 277, No. 4, pp. 1218-1229.
Guarnieri, M. et al., "Flexible versus rigid catheters for chronic administration of exogenous agents into central nervous system tissues", Journal of Neuroscience Methods, Elsevier Science Publisher B.V., Amsterdam, NL, vol. 144, No. 2, Jun. 2005, pp. 147-152.

* cited by examiner

Primary Examiner—Samir A Ahmed
Assistant Examiner—Atiba O Fitzpatrick
(74) Attorney, Agent, or Firm—Renner, Otto, Boisselle & Sklar, LLP

(57) ABSTRACT

A method for determining a backflow of a substance along a track of a delivery device includes: a) obtaining parameters that influence the flow of the fluid or substance; b) acquiring information about delivery data; and c) computing the backflow along the delivery device using the information in steps a) and b).

20 Claims, 2 Drawing Sheets

METHOD AND APPARATUS FOR DETERMINING A BACKFLOW OF A SUBSTANCE

RELATED APPLICATION DATA

This application claims priority of U.S. Provisional Application No. 60/754,508 filed on Dec. 28, 2005, which is incorporated herein by reference in its entirety.

FIELD OF THE INVENTION

The present invention relates to an apparatus and method for delivering agents and, more particularly, for intraparenchymal delivery of therapeutic agents in solution under positive pressure via infusion of the agents into a body or tissue. Further, the present invention relates to the planning of material delivery into tissue within a subject or patient, whereby the delivery of therapeutic, image enhancing, bio-active, pharmacological, nano-technical or otherwise active materials can be enhanced by calculating or simulating a backflow of the material flowing out of the delivery device.

BACKGROUND OF THE INVENTION

Devices to deliver a substance, such as injection or infusion devices, are known in the art and described, for example, in U.S. Pat. No. 5,720,720 and U.S. Pat. No. 6,572,579 B1.

Further, U.S. Pat. No. 6,549,803 B1 discloses the modeling of material in an organism by a uniformly structured field of static constants. US 2002/0114780 A1 discloses a method of increasing the volume of distribution of a therapeutic agent in a tissue in a subject during localized delivery.

SUMMARY OF THE INVENTION

The present invention provides an apparatus and method that improves Convection-enhanced drug delivery. Further, predictability and reliability of drug delivery is increased, for example, by accounting for backflow. Backflow is a phenomenon of fluid delivery wherein a fluid or other substance infused or injected through a delivery or infusion device, such as a catheter, cannula or needle, flows through one or more openings primarily at the tip or sides of the delivery device. After leaving the delivery device, the substance flows along an outer surface of the delivery device before it begins to significantly flow into the surrounding tissue. Backflow depends on various parameters, such as density or elasticity of the tissue surrounding the delivery device.

Infusion parameters, such as infusion rate, infusion material, geometry of the infusion device, etc. can be freely chosen and thus can vary from patient to patient. In many cases, diffusion of the substance into tissue significantly starts only after pressure on the tissue (which is caused by the backflow, e.g., the outflowing substance flowing in part back along the delivery device) is high enough to inhibit backflow along the catheter track, at which point the substance diffuses into the surrounding tissue. The length of this backflow can be several centimeters for catheters having a diameter of about one millimeter under clinical conditions. The present inventors have found that the region of backflow, rather than the catheter port(s), acts as the effective source of the infusion, controlling in large part the shape of the subsequent distribution of the substance in tissue.

Thus, since the backflow is strongly affected by the nature of the tissue surrounding the catheter, the tissue is accessed or tissue parameters are acquired, for example, by magnetic resonance imaging, subsequently employing the mathematics of backflow to estimate or even control the backflow length, wherein the process for planning the delivery (e.g., determining a location of an infusion device in tissue) can be based on the backflow characteristics, such as backflow length or shape, determined in advance or determined specifically for a patient.

The determination of the backflow includes determining and/or using one or more of the following parameters or characteristics:

the extension of the backflow, such as the length and/or shape of the backflow in various directions, as for example along the delivery device or catheter path;

the time dependent distribution or course of the substance exiting the delivery device;

the behavior or flow of the delivered substance; and/or the geometry or expansion or dilatation of the substance depending on the time after exiting the delivery device.

A method for determining backflow or parameters of backflow, such as the length of the backflow along a delivery device (e.g., a catheter or along a catheter track), includes obtaining parameters that influence the substance flow and acquiring the information about the delivery data. Information about the delivery data can include delivery parameters and/or information about the delivery device, such as the geometry or structure of the delivery device (e.g., catheter diameter, catheter profile) and/or properties of the substance or substances to be delivered (e.g., such as fluid properties including fluid viscosity, fluid molecular size) and/or parameters of the infusion (e.g., the flow rate and/or pressure).

Parameters that influence the substance flow, such as patient-specific data concerning the individual tissue structure, and the delivery data can be used to compute the backflow along the delivery device or catheter to determine or calculate the backflow. Depending on the parameters or data used to calculate the backflow, the length or region of the backflow can be determined and used as an effective source of the infusion for further simulation or control of the delivery parameters. These delivery parameters can include, for example, the number and placement of the catheters on a body. Additionally, the shape of the subsequent distribution of the infused substance in tissue can be simulated or even controlled.

The determination of backflow in terms of length or shape is significant for shaping or planing the subsequent infusion and thus, the infusion shapes and extents can be calculated or simulated based on the actual and probable time dependent shape or geometry of the backflow. The nature of the tissue influencing the backflow length or shapes can be considered by using patient-specific medical or anatomical data, for example, to determine the type of tissue surrounding the delivery device, such as gray matter, white matter or even the anisotropy of the tissue.

It is preferable that patient specific medical and/or anatomical data is acquired prior to the computation of the backflow. The patient specific medical data can include the diffusivity of water molecules, capillary permeability, blood flow or blood volume.

An apparatus for determining the backflow includes a medical imaging device for acquiring patient-specific medical, anatomical and/or physiological data, such as an imaging apparatus for obtaining MRI, CT, PET, SPECT and/or X-Ray images. This apparatus can be operatively coupled to a data processor or computer to receive the patient specific anatomical or medical data. The data processor can be operatively coupled to a database that includes information or parameters describing the influence of the patient specific data on the substance flow. The information or parameters can describe the behavior or characteristics of different types of tissue to specify or simulate, for example, the density, diffusivity, permeability or blood flow of or through each respective types of tissue. Furthermore, the database can include generalized information about parameters or properties of different types of tissue that may be obtained by experience, from literature, by modeling, studies, research or analysis. Additionally, the database can include parameters of the delivery device and/or properties of the substance to be delivered. The data processor operatively coupled to the imaging apparatus and the database then can compute the distance or shape of the backflow along the delivery device using the information obtained from the imaging device and preferably also based on the information obtained from the database. The calculated backflow then can be shown on a screen connected to the computer.

BRIEF DESCRIPTION OF THE DRAWINGS

The forgoing and other features of the invention are hereinafter discussed with reference to the drawings.

DETAILED DESCRIPTION

Figure 1:
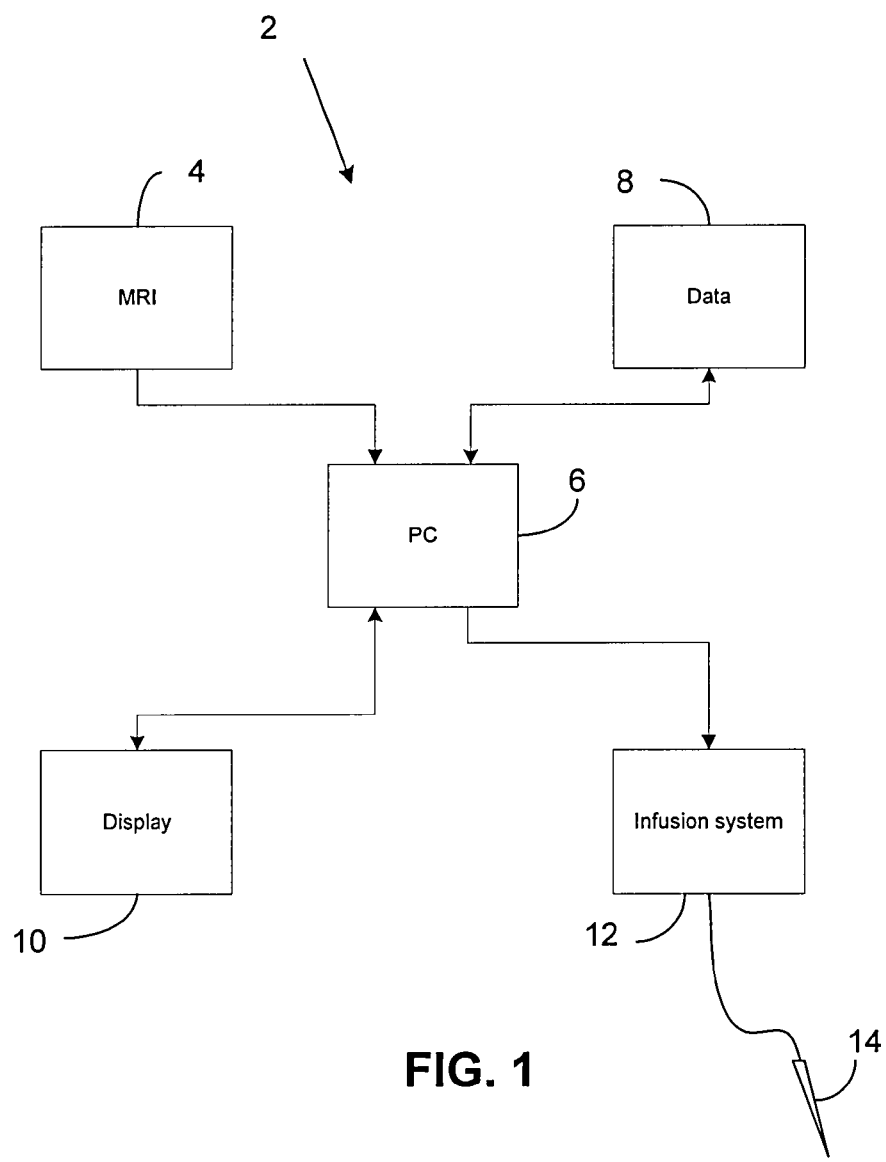
FIG. 1 shows an exemplary system for infusing substances according to the present invention.

FIG. 1 shows an exemplary infusion system 2, wherein an MRI apparatus 4 is used as a medical imaging device. The MRI apparatus 4 is operatively coupled to a computer 6, which enables the computer 6 to obtain patient-specific medical, anatomical and/or physiological data. The computer 6 also is operatively coupled to a data bank 8, which includes information on the properties of the tissue detected by the imaging device 4. This makes it possible to calculate parameters relevant for drug delivery using imaging data delivered by the imaging device 4, such as, for example, the permeability of a specific type of tissue, the metabolism in a specific tissue region or metabolism parameters of a substance to be delivered. Parameters for planning an infusion, such as the region of backflow, can be output to a display 10, such as a touch-screen or the like, which can be used as an input device for the computer 4 to input the selections of a user influencing the delivery plan, for example. Furthermore, the computer 6 is connected to an infusion system 12 including a reservoir (e.g., for the fluid to be infused) and a pump connected to a catheter 14. A navigation system (not shown), for example, can be used to determine placement and/or insertion of one or more catheters at a desired infusion site, or to control delivery parameters, such as the flow rate or pressure of the substance to be delivered by sending control signals (e.g., motor control signals) to the pumping device.

Figure 2:
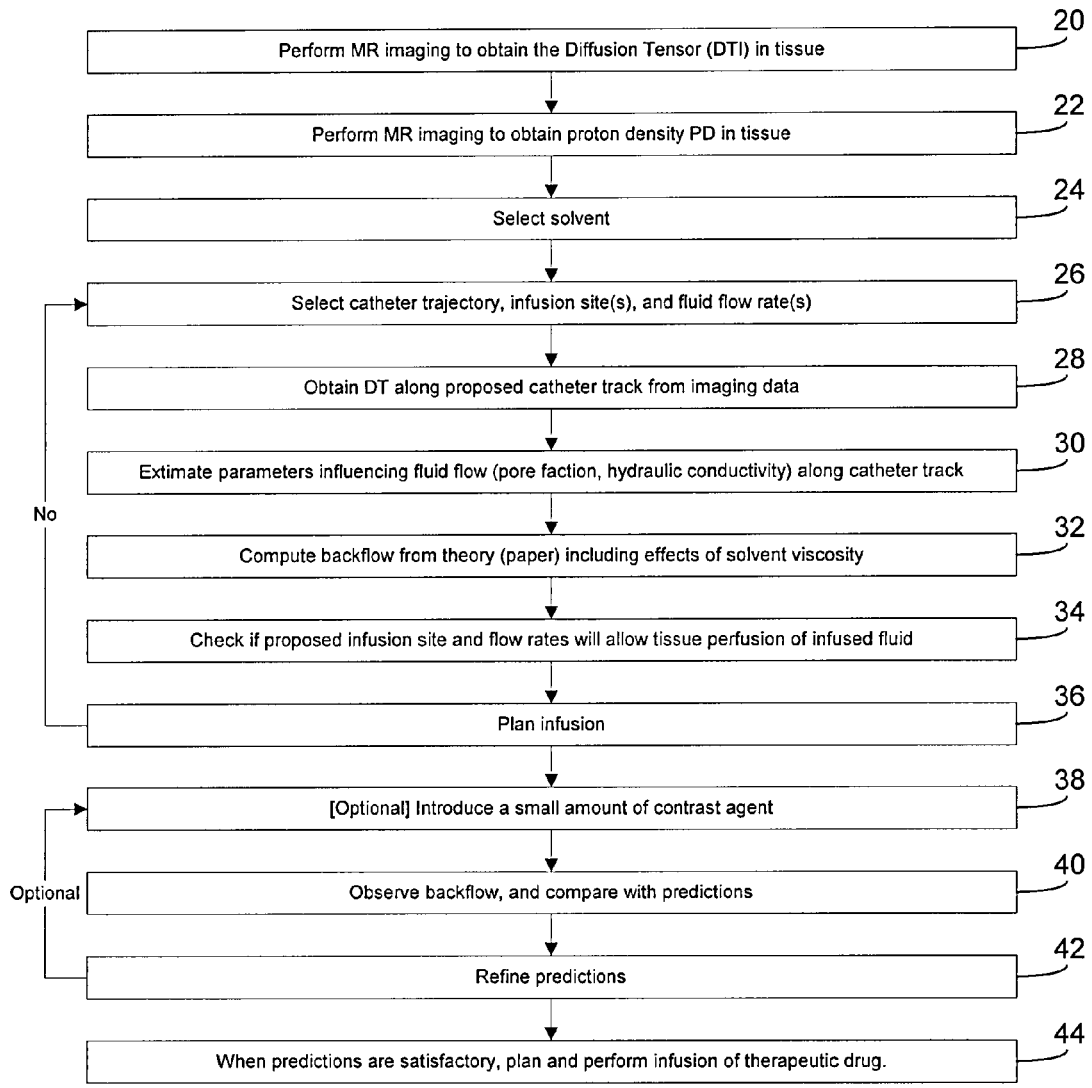
FIG. 2 shows a flow chart describing exemplary steps for infusing a substance in accordance with the present invention.

FIG. 2 shows a flow chart describing an exemplary implementation of the method, wherein at step 20 an MR image is taken to obtain the diffusion tensor DTI in tissue. Furthermore, the proton density PD in tissue is obtained from an MR image at step 22. The solvent to be infused is selected at step 24, preferably based on the information of the DTI and/or PD. At step 26, the catheter trajectory, infusion site(s) and fluid flow rate(s) are selected. From the imaging data the DT and PD are obtained at step 28, along a proposed catheter track. At step 30, parameters influencing the substance flow, such as pore fraction or hydraulic conductivity are estimated along the proposed catheter track. At step 32 the backflow is computed from theory including effects of the solvent viscosity to simulate the backflow shape, and at step 34 the proposed infusion site and flow rates are checked to determine if they will allow tissue perfusion of the infused substance. If this is possible, then at step 36 the infusion is planned. It this is not possible, then the method moves back to step 26 and a different catheter trajectory, a different infusion site and/or different substance flow rates are selected and the process to compute the backflow is repeated.

According to a preferred embodiment, a small amount of a contrast agent can be introduced at step 38 and at step 40 the backflow is observed and compared with the computed predicted backflow. At step 42 the result of the observation can be used to refine the predictions and to refine the infusion plan. When the predictions are satisfactory, the infusion of a therapeutic drug can be planned and performed, as indicated at step 44.

Figure 3:
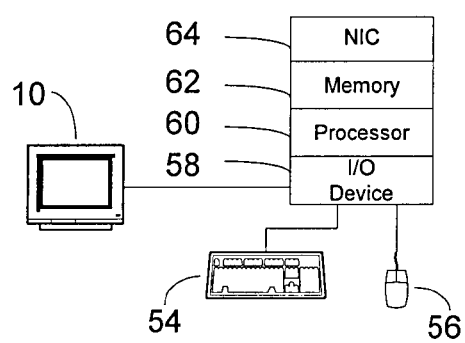
FIG. 3 is a block diagram of an exemplary computer system that can be used to carry out the method in accordance with invention.

FIG. 3 illustrates the computer 6, which may be used to implement the method described herein, in further detail. The computer 6 may include a display 10 for viewing system information, and, if the display is not a touch screen, a keyboard 54 and pointing device 56 for data entry, screen navigation, etc. A computer mouse or other device that points to or otherwise identifies a location, action, etc., e.g., by a point and click method or some other method, are examples of a pointing device 56. The display 10, keyboard 54 and mouse 56 communicate with a processor via an input/output device 58, such as a video card and/or serial port (e.g., a USB port or the like).

A processor 60, such as an AMD Athlon 64® processor or an Intel Pentium IV® processor, combined with a memory 62 execute programs to perform various functions, such as data entry, numerical calculations, screen display, system setup, etc. The memory 62 may comprise several devices, including volatile and non-volatile memory components. Accordingly, the memory 62 may include, for example, random access memory (RAM), read-only memory (ROM), hard disks, floppy disks, optical disks (e.g., CDs and DVDs), tapes, flash devices and/or other memory components, plus associated drives, players and/or readers for the memory devices. The processor 60 and the memory 62 are coupled using a local interface (not shown). The local interface may be, for example, a data bus with accompanying control bus, a network, or other subsystem.

The memory may form part of a storage medium for storing information, such as application data, screen information, programs, etc., part of which may be in the form of a database. The storage medium may be a hard drive, for example, or any other storage means that can retain data, including other magnetic and/or optical storage devices. A network interface card (NIC) 64 allows the computer 6 to communicate with other devices.

A person having ordinary skill in the art of computer programming and applications of programming for computer systems would be able in view of the description provided herein to program a computer system 6 to operate and to carry out the functions described herein. Accordingly, details as to the specific programming code have been omitted for the sake of brevity. Also, while software in the memory 62 or in some other memory of the computer and/or server may be used to allow the system to carry out the functions and features described herein in accordance with the preferred embodiment of the invention, such functions and features also could be carried out via dedicated hardware, firmware, software, or combinations thereof, without departing from the scope of the invention.

Computer program elements of the invention may be embodied in hardware and/or in software (including firmware, resident software, micro-code, etc.). The invention may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium such as the Internet. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for determining a backflow of a substance along a track of a delivery device placed within a patient, comprising:
   a) obtaining parameters that influence the flow of the substance;
   b) acquiring information about delivery data;
   c) computing, prior to infusion of the substance into the patient, the backflow along the delivery device using the information in steps a) and b); and
   d) using at least one of the computed backflow distance or shape to simulate further pressure fields, fluid concentration or flow parameters.

2. The method of claim 1, wherein obtaining parameters that influence the substance flow includes basing the parameters on the acquisition of at least one of patient specific medical data, anatomical data or generalized information from at least one of experience, literature, modeling, studies, research, or analysis.

3. The method according to claim 1, wherein acquiring information about delivery data includes acquiring the data from at least one of delivery parameters, delivery geometry or fluid properties.

4. The method according to claim 3, wherein delivery parameters include at least one of delivery device trajectory, flow rate, or pressure.

5. The method according to claim 3, wherein delivery geometry includes at includes at least one of catheter diameter or catheter profile.

6. The method according to claim 3, wherein fluid properties includes fluid viscosity or fluid molecular size.

7. The method according to claim 2, wherein basing the parameters on the acquisition of patient specific medical data includes using a medical imaging device to obtain at least one of the patient specific medical, anatomical data or generalized information.

8. The method according to claim 2, wherein basing the parameters on the acquisition of patient specific medical data includes using at least one of diffusivity of water molecules, capillary permeability, blood flow, or blood volume as the patient specific medical data.

9. The method according to claim 2, further comprising deriving from at least one of the patient-specific medical data or generalized information at least one of pore fraction, intracellular volume fraction, extracellular volume fraction, hydraulic conductivity, measures for blood brain barrier disruption, degradation rate, or washout of fluid.

10. The method according to claim 9, wherein deriving generalized information includes using at least one of literature values, properties about a target volume or an entire measurement volume of the patient specific medical information.

11. The method according to claim 9, wherein deriving from generalized information includes referring to a model for fluid distribution within tissue.

12. The method according to claim 9, wherein deriving from the generalized information includes using data from a database.

13. The method according to claim 2, further comprising using at least one of the patient-specific medical information data or generalized information to extract regions and/or structures including at least one of surfaces, functional areas, nerve fiber tracks, cavities, or intracranial structures that influence fluid flow and/or distribution.

14. The method according to claim 13, wherein extracting includes automatically or semi-automatically performing the extraction using at least one of models or algorithms for surface detection and delineation, atlases, anatomical information, or computerized versions thereof.

15. The method according to claim 1, wherein computing includes computing at least one of pore fraction, intracellular volume fraction, extracellular volume fraction, or hydraulic conductivity.

16. The method according to claim 1, further comprising computing the diffusivity of water molecules within a measurement volume.

17. The method according to claim 1, further comprising using the shape or length of the backflow to determine a location of an infusion device in tissue.

18. The method according to claim 17, further comprising computing the shape or distance of the backflow using altered data, devices, fluids or parameters to refine the determination or simulation of the backflow.

19. A computer program embodied on a non-transitory computer readable medium for determining a backflow of a substance along a track of a delivery device placed within a patient, comprising:
   a) code that obtains parameters that influence the flow of the substance;
   b) code that acquires information about delivery data;
   c) code that computes, prior to infusion of the substance into the patient, the backflow along the delivery device using the information in steps a) and b); and
   d) code that uses at least one of the computed backflow distance or shape to simulate further pressure fields, fluid concentration or flow parameters.

20. An apparatus for determining a backflow of a substance along a track of a delivery device placed within a patient, comprising:
   a processor and memory;
   logic stored in the memory and executable by the processor, said logic including
   a) logic that obtains parameters that influence the flow of the substance;
   b) logic that acquires information about delivery data;
   c) logic that computes, prior to infusion of the substance into the patient, the backflow along the delivery device using the information in steps a) and b); and
   d) logic that uses at least one of the computed backflow distance or shape to simulate further pressure fields, fluid concentration or flow parameters.

* * * * *